(12) United States Patent
Goral et al.

(10) Patent No.: US 12,029,999 B2
(45) Date of Patent: Jul. 9, 2024

(54) PACKAGE FOR BATCH CHROMATOGRAPHY

(71) Applicant: CORNING INCORPORATED, Corning, NY (US)

(72) Inventors: Vasiliy Nikolaevich Goral, Painted Post, NY (US); Ryann Loren Russell, Drexel Hill, PA (US)

(73) Assignee: CORNING INCORPORATED, Corning, NY (US)

( * ) Notice: Subject to any disclaimer, the term of this patent is extended or adjusted under 35 U.S.C. 154(b) by 1085 days.

(21) Appl. No.: 16/766,038

(22) PCT Filed: Nov. 30, 2018

(86) PCT No.: PCT/US2018/063203
§ 371 (c)(1),
(2) Date: May 21, 2020

(87) PCT Pub. No.: WO2019/108874
PCT Pub. Date: Jun. 6, 2019

(65) Prior Publication Data
US 2020/0360838 A1 Nov. 19, 2020

Related U.S. Application Data

(60) Provisional application No. 62/640,190, filed on Mar. 8, 2018, provisional application No. 62/592,983, filed on Nov. 30, 2017.

(51) Int. Cl.
*B01D 15/22* (2006.01)
*B01D 15/20* (2006.01)
(Continued)

(52) U.S. Cl.
CPC ........... *B01D 15/22* (2013.01); *B01D 15/206* (2013.01); *B01D 15/424* (2013.01); *C12M 47/10* (2013.01);
(Continued)

(58) Field of Classification Search
CPC ........ B01D 15/42; B01D 15/20; B01D 15/22; B01D 15/203; C07K 1/18; C07K 1/22; C12N 9/90; C12N 9/24
See application file for complete search history.

(56) References Cited

U.S. PATENT DOCUMENTS 8,183,035 B1 5/2012 Niazi
2008/0142439 A1 6/2008 Berglof et al.
(Continued)

FOREIGN PATENT DOCUMENTS

CN 1791439 A 6/2006
CN 102740948 A 10/2012
(Continued)

OTHER PUBLICATIONS

Japanese Patent Application No. 2020-529323, Office Action, dated May 17, 2023, 7 pages (3 pages of English Translation and 4 pages of Original); Japanese Patent Office.
(Continued)

*Primary Examiner* — Walter D. Griffin
*Assistant Examiner* — Cameron J Allen
(74) *Attorney, Agent, or Firm* — Chandra J. Duncan

(57) ABSTRACT

A method for separating at least one target compound from a feed solution is provided. The method includes filling a bioprocess package with a chromatography resin. The bioprocess package includes a 2D flexible container comprising an interior compartment, a height having an upper half and a lower half, an inlet and an outlet, the inlet and the outlet being disposed on the same half of the 2D flexible container,
(Continued)

the channel-forming feature being configured to maintain a fluid flow path that fluidly connects the interior compartment of the flexible container with the outlet. The method further includes flowing a feed solution into the bioprocess package to contact the chromatography resin such that substantially all of the at least one target compound binds to the chromatography resin, washing the chromatography resin in the bioprocess package, and eluting the chromatography resin.

24 Claims, 10 Drawing Sheets

(51) Int. Cl.
  *B01D 15/42* (2006.01)
  *C12M 1/00* (2006.01)
  *G01N 30/56* (2006.01)
  *G01N 30/60* (2006.01)

(52) U.S. Cl.
  CPC ........... *G01N 30/56* (2013.01); *G01N 30/606* (2013.01); *G01N 2030/562* (2013.01)

(56) References Cited

U.S. PATENT DOCUMENTS

| | | | |
|---|---|---|---|
| 2008/0274536 A1* | 11/2008 | Hatano | C12M 23/34 |
| | | | 435/243 |
| 2010/0095843 A1 | 4/2010 | Gebert et al. | |
| 2011/0198286 A1 | 8/2011 | Niazi | |
| 2012/0149885 A1 | 6/2012 | Niazi | |
| 2012/0258519 A1* | 10/2012 | Niazi | C07K 1/22 |
| | | | 530/382 |
| 2013/0248451 A1 | 9/2013 | Hall et al. | |
| 2014/0158631 A1* | 6/2014 | Govind | B01D 17/0205 |
| | | | 252/60 |
| 2015/0202595 A1 | 7/2015 | Godawat et al. | |
| 2015/0292991 A1 | 10/2015 | Cacace | |
| 2016/0145567 A1 | 5/2016 | Henry et al. | |
| 2016/0166949 A1* | 6/2016 | Niazi | C07K 1/20 |
| | | | 530/413 |

FOREIGN PATENT DOCUMENTS

| | | |
|---|---|---|
| CN | 103221105 A | 7/2013 |
| EP | 1260518 A1 | 11/2002 |
| JP | 2008-533464 A | 8/2008 |
| JP | 2014-527808 A | 10/2014 |
| JP | 2017-508135 A | 3/2017 |
| WO | WO-9532783 A1 * | 12/1995 ............. A01N 25/02 |
| WO | 2001/064711 A1 | 9/2001 |
| WO | 2009/016431 A1 | 2/2009 |
| WO | 2017/116910 A1 | 7/2017 |
| WO | 2017/189218 A2 | 11/2017 |

OTHER PUBLICATIONS

International Search Report and Written Opinion of the International Searching Authority; PCT/US2018/063203; dated Feb. 27, 2019; 10 Pages; European Patent Office.

Pall, "Biotech—Continuosly Improving Bioprocesses", Available Online at <https://www.pall.com/en/biotech.html>, 2020, 6 pages.

Chinese Patent Application No. 201880085795.7, Office Action dated Feb. 16, 2023, 5 pages (English Translation only), Chinese Patent Office.

\* cited by examiner

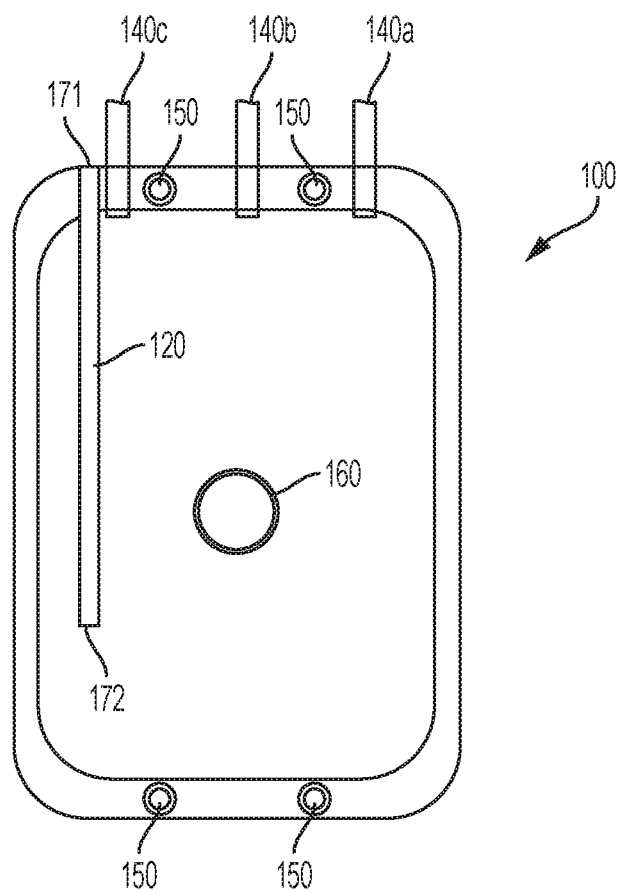
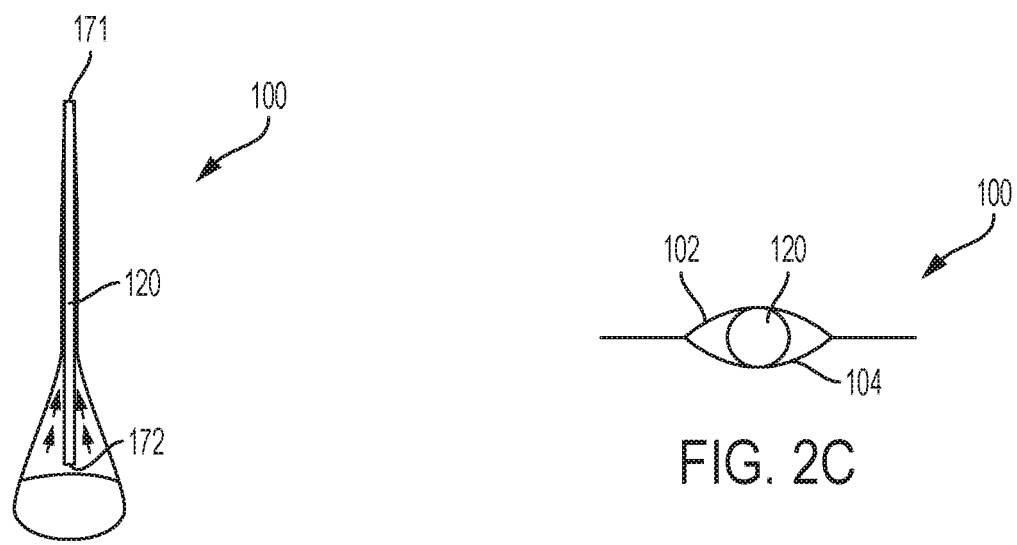
FIG. 2A
FIG. 2B
FIG. 2C

PACKAGE FOR BATCH CHROMATOGRAPHY

CROSS-REFERENCE TO RELATED APPLICATIONS

This is a national stage application under 35 U.S.C. § 371 of International Application No. PCT/US2018/063203, filed on Nov. 30, 2018, which claims the benefit of priority under 35 U.S.C § 120 of U.S. Provisional Application Ser. No. 62/640,190 filed on Mar. 8, 2018, and U.S. Provisional Application Ser. No. 62/592,983 filed on Nov. 30, 2017, the contents of which are relied upon and incorporated herein by reference in their entirety.

FIELD

The present disclosure generally relates to bioprocess bags for batch chromatography and systems employing the same. In particular, the present disclosure relates to bioprocess bags for batch chromatography having a channel-forming feature that facilitates removal of fluid and/or other components from the interior compartment of the bags.

BACKGROUND

There has been significant and sustained growth in new drug production featuring, for example, monoclonal antibodies and other proteins. This growth is due to expanding drug pipelines, as well as more efficient cell lines and bioreactor growth optimizations. Downstream purification, often including chromatography, is a part of the drug production process where the most significant investments of time and resources are consumed. Chromatography is a process to separate product from contaminating species and is an important step in drug production and other bioprocessing applications. However, there have been few improvements made to the column chromatography processes. In particular, the processes have not been improved to account for improvements in upstream technology that allow for increased volumes to be processed for longer periods of time. While these results are considered advantageous for several reasons, the improvements are also generally leading to the production of more impurities in the bioprocessing systems which could benefit from downstream chromatography methods and systems that can perform separation of higher volumes in an efficient manner. Additionally, conventional chromatography methods and systems have physical limitations which limit the ability to scale up the methods and systems. The largest chromatography columns currently available on the market would require multiple chromatography cycles to perform separation of only a portion (for example, as 10 g/L of product) of the volume of a single bioreactor. Such separation could take as long as 24 hours and cause a significant bottleneck in the overall drug production process.

Bags containing fluids under sterile conditions are used in the bioprocessing industry for the formulation, storage, transfer and transport of fluid while maintaining sterile conditions. Some of the characteristics of the bags to preserve the quality of the products contained within include biocompatibility with the products, sterility, and non-pyrogenicity. The bags are typically disposed of after use and are recognized as efficient means to prepare and store sterile fluids. Generally, these disposable bioprocessing bags are flexible and made from compatible plastic that is sterilized by Gamma radiation. The bags can be used for all bioprocessing applications including, but not limited to, formulating, filling, storing and transporting final product, stocking pharmaceuticals in cold storage or deep freeze and for sampling and analytical purposes. The bags may also provide an environment for cell culture. Additionally, the bags may be used for biological fluids such as serum, buffers, and ultrapure water and also for growing cell cultures to obtain the valuable biopharmaceutical compounds produced by cells. With regard to chromatography processes, disposable products are beginning to find greater use as the disposable products generally save labor and do not require cleaning. However, disposable products continue to adhere to the design features of conventional column methods and systems.

SUMMARY

According to an embodiment of the present disclosure, a method for separating at least one target compound from a feed solution is provided. The method includes filling a bioprocess package with a chromatography resin. The bioprocess package includes a 2D flexible container comprising an interior compartment, a height having an upper half and a lower half, an inlet and an outlet, the inlet and the outlet being disposed on the same half of the 2D flexible container, and a channel-forming feature in the interior compartment of the container, the channel-forming feature being configured to maintain a fluid flow path that fluidly connects the interior compartment of the flexible container with the outlet. The method further includes flowing a feed solution into the bioprocess package to contact the chromatography resin such that substantially all of the at least one target compound binds to the chromatography resin, washing the chromatography resin in the bioprocess package, and eluting the chromatography resin such that substantially all of the at least one target compound is released from the chromatography resin.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

The disclosure will be understood more clearly from the following description and from the accompanying figures, given purely by way of non-limiting example, in which:

FIG. 2A is a schematic illustration of a bioprocess bag having a channel-forming feature in accordance with embodiments of the present disclosure;

FIG. 2B is a schematic illustration showing a side view of the bioprocess bag having a channel-forming feature of FIG. 2A;

FIG. 2C is a schematic illustration showing an enlarged and exaggerated top view of the bioprocess bag having a channel-forming feature of FIG. 2B;

DETAILED DESCRIPTION

Figure 1:
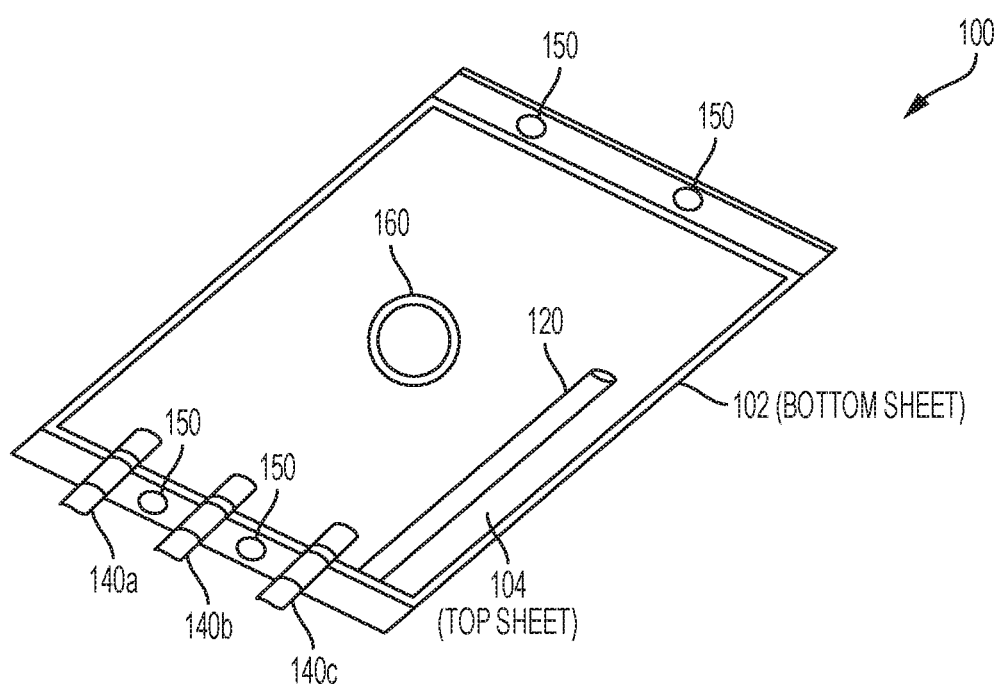
FIG. 1 illustrates an exemplary bioprocess bag having a channel-forming feature in accordance with embodiments of the present disclosure.

Reference will now be made in detail to the present embodiment(s), an example(s) of which is/are illustrated in the accompanying drawings. Whenever possible, the same reference numerals will be used throughout the drawings to refer to the same or like parts.

The singular forms "a," "an" and "the" include plural referents unless the context clearly dictates otherwise. The endpoints of all ranges reciting the same characteristic are independently combinable and inclusive of the recited endpoint. All references are incorporated herein by reference.

As used herein, "have," "having," "include," "including," "comprise," "comprising" or the like are used in their open ended sense, and generally mean "including, but not limited to."

All scientific and technical terms used herein have meanings commonly used in the art unless otherwise specified. The definitions provided herein are to facilitate understanding of certain terms used frequently herein and are not meant to limit the scope of the present disclosure.

The present disclosure is described below, at first generally, then in detail on the basis of several exemplary embodiments. The features shown in combination with one another in the individual exemplary embodiments do not all have to be realized. In particular, individual features may also be omitted or combined in some other way with other features shown of the same exemplary embodiment or else of other exemplary embodiments.

Embodiments of the present disclosure relate to bioprocess bags. The bioprocess bags described herein are 2D bags formed from flexible materials. As used herein, the term "2D bag" refers to a flat, rectangular, "pillow-style" bag formed by seaming together two flexible sheets. Bioprocess bags in accordance with embodiments of the present disclosure are formed from disposable materials and may be discarded after a single use, thereby eliminating washing/sterilizing operations as well as maintenance associated with conventional cell culture vessels. The bioprocess bags described herein advantageously allow for aseptically transferring the feed solution from a cell culture vessel, such as a bioreactor, to the bag where batch chromatography can be performed in a single vessel. With the bioprocess bags described herein, such actions can be taken without exposing the desired product to the surrounding atmosphere.

FIG. 1 illustrates a bioprocess bag in accordance with embodiments of the present disclosure. As shown, the bioprocess bag 100, 1100 includes at least two sheets 102, 104 formed from films or laminates. The sheets 102, 104 are hermetically sealed (for example by welding or by an adhesive) along the edges of the sheets to form a pillow-shaped bag having an interior compartment for receiving fluid. The bioprocess bag 100, 1100 preferably provides a closed system for use in all phases of processing fluid and/or other components. FIG. 1 illustrates an exemplary configuration of a bioprocess bag formed from two sheets 102, 104 that are longer than they are wide and, when attached along their edges, form a bioprocess bag 100, 1100 having two sides, a top and a bottom where the two sides are longer than the top and the bottom are wide. It should be understood that this is just an exemplary configuration, and that the bioprocess bag as described herein may have a top, a bottom and two sides having equal lengths. The bioprocess bag 100, 1100 is described herein as having two sides, a top and a bottom. However, it should be understood that the terms "top", "bottom", "side" and the like are used herein for descriptive purposes and not necessarily for describing permanent relative positions. It should be understood that the terms so used are interchangeable under appropriate circumstances such that embodiments of the present disclosure are, for example, capable of operation in other orientations than those illustrated or otherwise described herein.

Each of the sheets 102, 104 of the bioprocess bag 100, 1100 may be formed from one or more of the same or different materials. Such materials are those conventionally associated with disposable products for bioprocess applications. Any or all of the sheets 102, 104 of the bioprocess bag 100, 1100 may be formed from a film or laminate that includes at least one plastic material from the following group: polyethylene (PE), polypropylene (PP), polyvinyl chloride (PVC), polyethylene terephtalate (PET), polystyrene (PS), polycarbonate (PC), polymethylpentene (PMP), polyetheretherketone (PEEK) polytetrafluoroethylene (PTFE), polyfluoroalkoxy (PFA), polychlorotrifluoroethylene (PCTFE), ethylene vinyl acetate (EVA), and derivatives thereof.

It should be understood that the dimensions of the bioprocess bag 100, 1100 including both relative and absolute dimensions can be varied. For example, the bags may be configured to hold a volume of fluid and/or other components of about 1.0 mL, or about 5.0 mL, or about 10 mL, or about 25 mL, or about 50 mL, or about 100 mL, or about or about 250 mL, or about 500 mL, or about 1.0 L, or 5.0 L, or about 10 L, or about 50 L, or about 100 L, or about 150 L or even about 200 L, as well as all volumes therein between.

Total thickness of the film or laminate may be selected, for example, based on the desired gas permeability of the bioprocess bag 100, 1100 or based on the desired rigidity or flexibility of the bag 100, 1100. For example, the thickness of sheets 102, 104 may be between about 0.002 inches and about 1.5 inches. As described herein, the thickness of sheet 102 and sheet 104 may be the same or different.

The bioprocess bag 100, 1100 is hermetically sealed and may have one or more openings for introducing or recovering fluid and/or other components. Where the bioprocess bag 100, 1100 includes one or more openings, the one or more openings may include seals that in a first configuration expose the one or more openings to aseptic fluid communication between an external container and the interior compartment of the bag through the opening. In a second configuration, the seals close the one or more openings and prevent or reduce fluid communication between the outside of the bag and the interior compartment of the bag through the opening. The seals may take any desired form, including, but not limited to, a clamp, tape, a cap, a tube portion having a welded end, a zipper, a slide zipper, interlocking or coupling structures, aseptic connectors and the like.

Bioprocess bags 100, 1100 as described herein include at least one connection apparatus which includes an internal fluid passage that permits the flow of fluids and/or other components into or out of the interior compartment of the bioprocess bag 100, 1100. With further reference to FIG. 1, the at least one connection apparatus may be at least one connector 140 which includes an internal fluid passage that permits the flow of fluids and/or other components into or out of the interior compartment of the bioprocess bag 100. The at least one connector 140 includes a proximal end and a distal end and extends through an opening formed in a portion of the sealed edge of the bioprocess bag 100. The proximal end of the at least one connector 140 may extend through the opening and into the interior compartment of the bioprocess bag 100. Alternatively, without extending into the interior compartment of the bioprocess bag 100, the proximal end of the at least one connector 140 may be positioned in the opening such that flow of fluids and/or other components into or out of the interior compartment of the bioprocess bag 100 is permitted. At least a portion of the film or laminate of the sheets 102, 104 is heat sealed, or otherwise adhered, around the at least one connector 140 such that the bioprocess bag 100 is hermetically sealed.

Figure 11A:
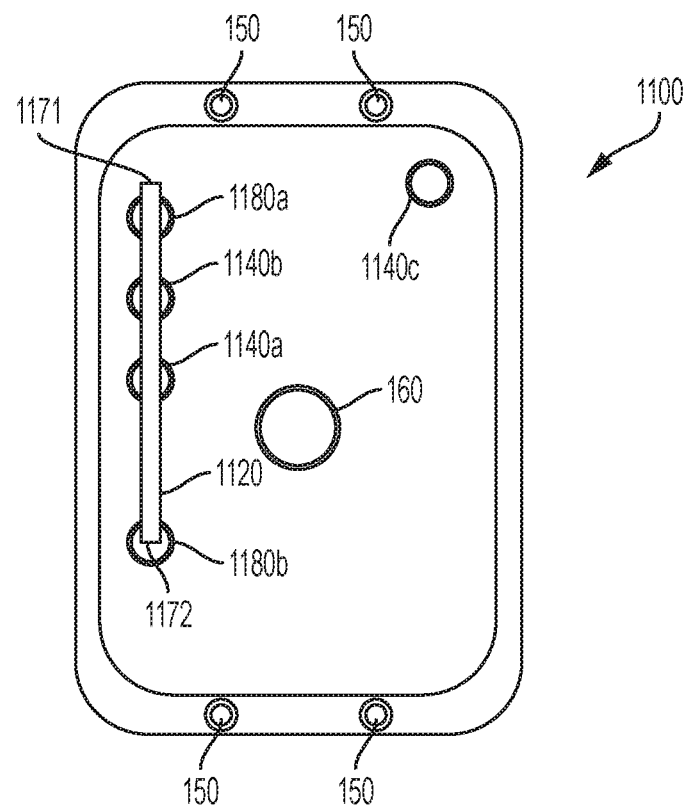
FIG. 11A is a schematic illustration of a bioprocess bag having a channel-forming feature in accordance with embodiments of the present disclosure.
Figure 11B:
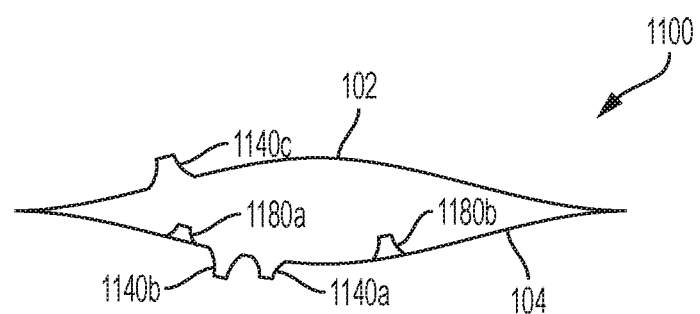
FIG. 11B is a schematic illustration showing a side view of a bioprocess bag having a channel-forming feature of FIG. 11A.
Figure 12:
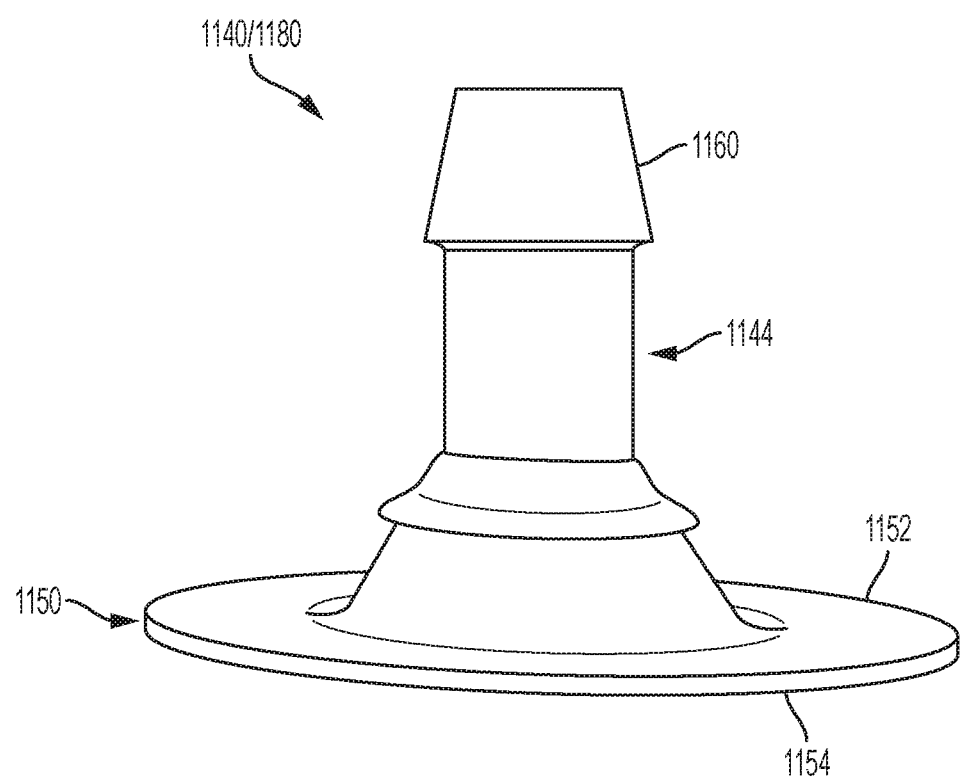
FIG. 12 illustrates an exemplary face port in accordance with embodiments of the present disclosure.

With reference to FIGS. 11A and 11B, the at least one connection apparatus may be at least one outwardly facing face port 1140 which includes an internal fluid passage that permits the flow of fluids and/or other components into or out of the interior compartment of the bioprocess bag 1100. The outwardly facing face port 1140 may be formed in a face of at least one of sheets 102, 104. As shown in FIG. 12, the at least one face port 1140 may include a base flange 1150 having a top surface 1152 and a bottom surface 1154. At least a portion of the film or laminate of one of sheet 102 and sheet 104 is welded, heat sealed, or otherwise adhered to the base flange 1150 of at least one face port 1140 such that the bioprocess bag 1100 is hermetically sealed. The at least one face port 1140 further includes an extension 1144 that extends a predetermined length from the base flange 1150 and is configured to engage an open end of a length of tubing. The extension 1144 may include a coupler, such as a barb 1160, at one end to facilitate engagement with an open end of tubing. According to embodiments of the present disclosure, the at least one face port 1140 is configured such that the extension 1144 extends to an external side of the bioprocess bag 1100 and not into the interior compartment of the bioprocess bag 1100. One of sheet 102 and sheet 104 may be welded, heat sealed, or otherwise adhered to the top surface 1152 of the base flange 1150. Alternatively, one of sheet 102 and sheet 104 may be welded, heat sealed, or otherwise adhered to the bottom surface 1154 of the base flange 1150. As used herein, the term "face port" refers to a port that is located on the face of at least one of sheet 102 and sheet 104 rather than on an edge or seam of the bioprocess bag 100, 1100. Also as used herein, the term "outwardly facing face port" refers to a face port having an extension which extends from a sheet to an external side of the bioprocess bag and not into the interior compartment of the bioprocess bag. In contrast, as used herein, the term "inwardly facing face port" refers to a face port having an extension which extends from a sheet to into the interior compartment of the bioprocess bag.

The at least one connector 140 or the at least one face port 1140 may be a relatively rigid plastic component formed from, for example, but not limited to, high density polypropylene (HDPP), polypropylene, high density polyethylene (HDPE), polyethylene, EVA, LDPE and LLDPE. Optionally, the at least one connector 140 may be flexible plastic tubing. Where the at least one connector 140 is a relatively rigid plastic component, the distal end of the at least one connector 140 is configured to engage an open end of a length of tubing which aseptically fluidly connects the at least one connector 140 to a separate length of tubing (i.e., through an aseptic connector) or to a connection apparatus of an external container. Similarly, where the at least one face port 1140 is a relatively rigid plastic component, the extension 1144 is configured to engage an open end of a length of tubing which aseptically fluidly connects the at least one face port 1140 to a separate length of tubing (i.e., through an aseptic connector) or to a connection apparatus of an external container. Where the at least one connector 140 is flexible plastic tubing, the at least one connector 140 may be aseptically fluidly connected to a separate length of tubing (i.e., through an aseptic connector) or to a connection apparatus of an external container. The seals described above may interact with, or be connected to, the at least one connector 140, the extension 1144 and/or the separate length of tubing to selectively permit or prevent fluid communication between the interior compartment of the bag 100, 1100 and an external container.

The bioprocess bag 100 may include a plurality of connectors 140, such as connectors 140a, 140b and 140c shown, for example, in FIG. 1. The dimensions of the plurality of connectors 140 may be equal, or the dimensions of each of the plurality of connectors 140 may vary. It is also contemplated that the dimensions of at least two of the plurality of connectors 140 may be equal and at least one other of the plurality of connectors 140 differs from the dimensions of the at least two of the plurality of connectors 140. Where the at least one connector 140 is a relatively rigid plastic connector, the at least one connector 140 may include a coupler configured to hold the at least one connector 140 in the bioprocess bag 100. The coupler may be a portion having any shape that extends from an outer wall of the at least one connector 140 around which portions of the film or laminate of sheets 102, 104 may be heat sealed. The coupler may be, for example, a barb, a plastic ring, or a plastic flange. The coupler may be integrally formed with the at least one connector 140 or may be separately formed and attached to the at least one connector 140. Where the bioprocess bag 100 includes a plurality of connectors 140a, 140b, 140c with a first of the connectors 140 being an inlet and a second of the connectors 140 being an outlet, the inlet and the outlet are arranged on the same side of the bioprocess bag 100 (i.e., at the top of the bag). Optionally, a bioprocess bag 100 having more than two connectors 140 may include any number of connectors 140 arranged on any side of the bioprocess bag 100 so long as two of the connectors 140 are located on the same side of the bag with a first of the two connectors 140 being an inlet and a second of the two connectors 140 being an outlet. Referring once again to FIG. 1 as an example, connector 140a may be an inlet and connector 140c may be an outlet.

The bioprocess bag 1100 may include a plurality of face ports 1140, such as face ports 1140a, 1140b and 1140c shown, for example, in FIGS. 11A and 11B. The dimensions of the plurality of face ports 1140 may be equal, or the dimensions of each of the plurality of face ports 1140 may vary. It is also contemplated that the dimensions of at least two of the plurality of face ports 1140 may be equal and at least one other of the plurality of face ports 1140 differs from the dimensions of the at least two of the plurality of face ports 1140. Where the bioprocess bag 1100 includes a plurality of face ports 1140a, 1140b, 1140c with a first of the face ports 1140 being an inlet and a second of the face ports 1140 being an outlet, the inlet and the outlet are arranged on the same half of the height of the bioprocess bag 1100 (i.e., an upper half of a sheet 102, 103 of the bag). Optionally, a bioprocess bag 1100 having more than two face ports 1140 may include any number of face ports 1140 arranged on any side of the bioprocess bag 1100 so long as two of the face ports 1140 are located on the same side of the bag with a first of the two face ports 1140 being an inlet and a second of the two face ports 1140 being an outlet. Referring once again to FIGS. 11A and 11B as an example, face port 1140a may be an inlet and face port 1140b may be an outlet.

Figure 5:
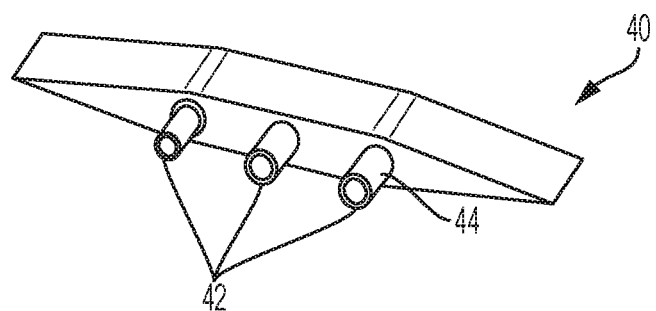
FIG. 5 illustrates an exemplary port fitment in accordance with embodiments of the present disclosure.
Figure 6:
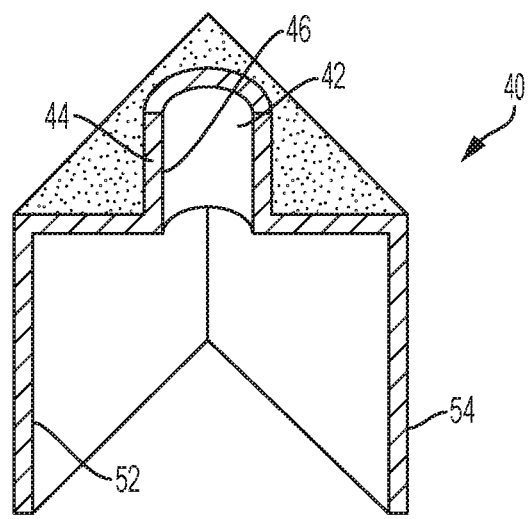
FIG. 6 illustrates a cross section of an exemplary port fitment in accordance with embodiments of the present disclosure.

According to embodiments of the present disclosure, the at least one connection apparatus may be a port fitment 40, such as the port fitment 40 shown in FIG. 5, having at least one port 42 that permits the flow of fluids and/or other components into or out of an interior compartment of the bioprocess bag 100. As shown in FIG. 6, the at least one port 42 is in fluid communication with an interior passage of an extension 44 that extends a predetermined length from an opening of the at least one port 42 and is configured to engage an open end of a length of tubing. The extension 44 may include a coupler, such as a barb, at one end to facilitate engagement with an open end of tubing. The port fitment 40 may include a plurality of ports 42. The dimensions of the plurality of ports 42 may be equal for each of the plurality of ports 42, or the dimensions of each of the plurality of ports 42 may vary. It is also contemplated that the dimensions of at least two of the plurality of ports 42 may be equal and at least one other of the plurality of ports 42 differs from the dimensions of the at least two of the plurality of ports 42. According to embodiments of the present disclosure, the port fitment 40 may be any shape. The exemplary port fitment 40 illustrated in the figures is a boat shaped port fitment, but the port fitment 42 disclosed herein is not so limited. The port fitment 40 may be a plastic port fitment formed from, for example, but not limited to, high density polypropylene (HDPP), polypropylene, high density polyethylene (HDPE), polyethylene, EVA, LDPE and LLDPE.

Connection is formed between a polymer layer of the film or laminate of the sheets 102, 104 and the port fitment 40 to form a hermetic seal between the bag 100 and the port fitment 40. As shown in FIG. 6, the port fitment 40 includes an exterior surface 54 and an interior surface 52. Connection between the bioprocess bag 100 and the port fitment 40 may be along any one of the exterior surface 54 and the interior surface 52. The connection may be made by welding or any other type of attachment, such that, with the exception of the at least one port 42, a fluid-impervious seal is formed between the port fitment 40 and the bioprocess bag 100.

According to embodiments of the present disclosure, the bioprocess bag 100, 1100 includes a channel-forming feature. A problem encountered when dispensing the contents of flexible bags is that portions of the sheets of the bags can collapse into contact with each other to form sealed pockets as the volume of the bag shrinks. The channel-forming feature described herein prevents the sheets 102, 104 of the bioprocess bag 100, 1100 from sealing off portions of the bag 100, 1100 and/or from isolating the fluid and/or other components in the bag 100, 1100 from reaching an outlet. The channel-forming feature prevents the bag 100, 1100 from closing on itself, thus providing a fluid flow path for the contents of the bag 100, 1100 to reach an outlet.

As shown in FIGS. 2A-2C, the channel-forming feature as described herein may be a solid extruded plastic component 120 that extends from a first end 171 to a second end, 172 the second end 172 being disposed in the interior compartment of the bioprocess bag 100. The first end 171 of the solid extruded plastic component 120 may be welded into a seam of the bioprocess bag 100, for example, into the top seam of the bioprocess bag 100. Alternatively, the first end 171 of the solid extruded plastic component 120 may be disposed in one of the plurality of connectors 140. Similarly, where the at least one connection apparatus is a port fitment 40 as described herein, the first end 171 of the solid extruded plastic component 120 may be disposed within one of the plurality of ports 42. The solid extruded plastic component 120 extends into the interior compartment of the bioprocess bag 100 a distance sufficient to prevent the sheets 102, 104 of the bioprocess bag 100 from sealing off portions of the bag 100 and/or from isolating the fluid and/or other components in the bag 100 from reaching an outlet. According to embodiments of the present disclosure, the solid extruded plastic component 120 may have a length such that it spans at least about half the distance between the top of the bioprocess bag 100 and the bottom of the bioprocess bag 100. In other words, the solid extruded plastic component 120 may have a length that is at least about half the length of the sheets 102, 104 of the bioprocess bag 100, but preferably less than the full length of the sheets 102, 104 of the bioprocess bag 100. For example, where the length of the sheets 102, 104 is represented by "L", the solid extruded plastic component 120 may have a length that is between about 0.5 L and about 0.95 L, or between about 0.5 L and about 0.85 L, or even between about 0.5 L and about 0.75 L. The solid extruded plastic component 120 may have any cross-sectional shape such as round, square or rectangular. The solid extruded plastic component 120 may also have a shape that advantageously provides additional channels through which fluid may flow. For example, the solid extruded plastic component 120 may have a star-shaped cross-section.

Figure 3A:
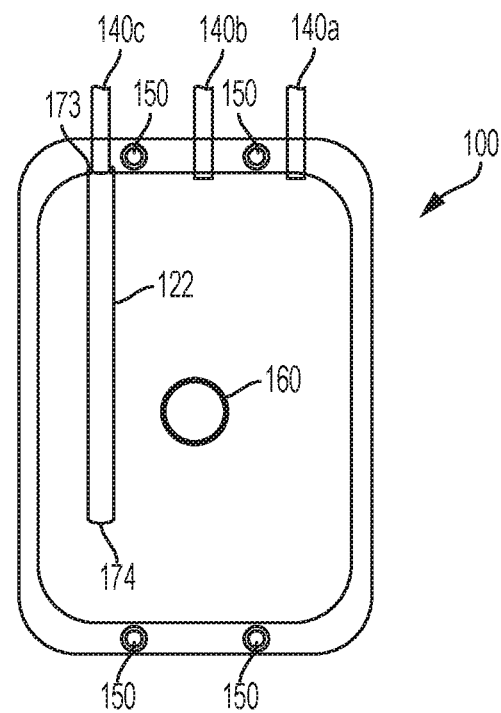
FIG. 3A is a schematic illustration of a bioprocess bag having a channel-forming feature in accordance with embodiments of the present disclosure.
Figure 3B:
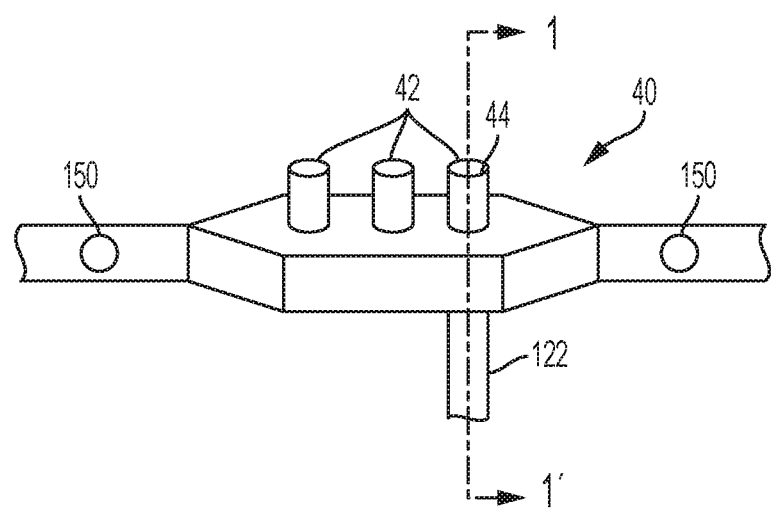
FIG. 3B is a schematic illustration of a port fitment having a channel-forming feature attached thereto in accordance with embodiments of the present disclosure.
Figure 3C:
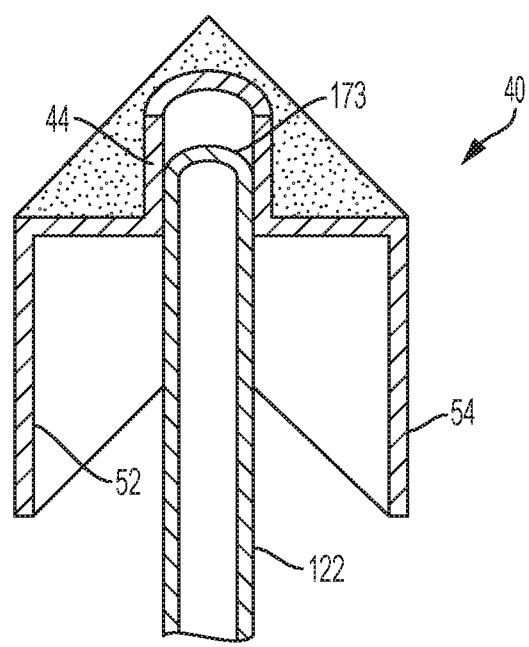
FIG. 3C is a cross sectional view of the port fitment of FIG. 3B sectioned along line 1-1' of FIG. 3B.

As shown in FIGS. 3A-3C, the channel-forming feature as described herein may be a tubular plastic component 122 (such as a portion of tubing) that extends from a first end 173 to a second end 174, the second end 174 being disposed in the interior compartment of the bioprocess bag 100. The first end 173 of the tubular plastic component 122 may be welded into a seam of the bioprocess bag 100, for example, into the top seam of the bioprocess bag 100. Alternatively, as shown in FIG. 3A, the first end 173 of the tubular plastic component 122 may be attached to, or disposed in, one of the plurality of connectors 140. Similarly, as shown in FIGS. 3B and 3C, where the at least one connection apparatus is a port fitment 40 as described herein, the first end 173 of the tubular plastic component may be attached to, or disposed within, one of the plurality of ports 42. Such arrangement also allows the channel-forming feature to form a conduit which cannot be closed off by exertion of a pressure on sheets 102, 104 as the bioprocess bag 100 collapses. The second end 174 of the tubular plastic component 122 may be a closed end, or may include a plug inserted in the end of the tubular plastic component 122 to isolate the interior of the tubular plastic component 122 from the contents of the interior compartment of the bioprocess bag 100. The tubular plastic component 122 extends into the interior compartment of the bioprocess bag 100 a distance sufficient to prevent the sheets 102, 104 of the bioprocess bag 100 from sealing off portions of the bag 100 and/or from isolating the fluid and/or other components in the bag 100 from reaching an outlet. According to embodiments of the present disclosure, the tubular plastic component 122 may have a length such that it spans at least about half the distance between the top of the bioprocess bag 100 and the bottom of the bioprocess bag 100. In other words, the tubular plastic component 122 may have a length that is at least about half the length of the sheets 102, 104 of the bioprocess bag 100, but preferably less than the full length of the sheets 102, 104 of the bioprocess bag 100. For example, where the length of the sheets 102, 104 is represented by "L", the tubular plastic component 122 may have a length that is between about 0.5 L and about 0.95 L, or between about 0.5 L and about 0.85 L, or even between about 0.5 L and about 0.75 L.

Figure 4A:
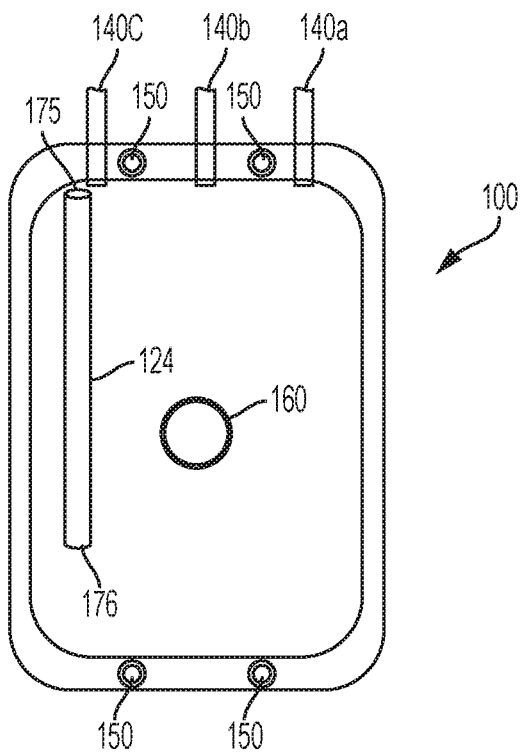
FIG. 4A is a schematic illustration of a bioprocess bag having a channel-forming feature in accordance with embodiments of the present disclosure.
Figure 4B:
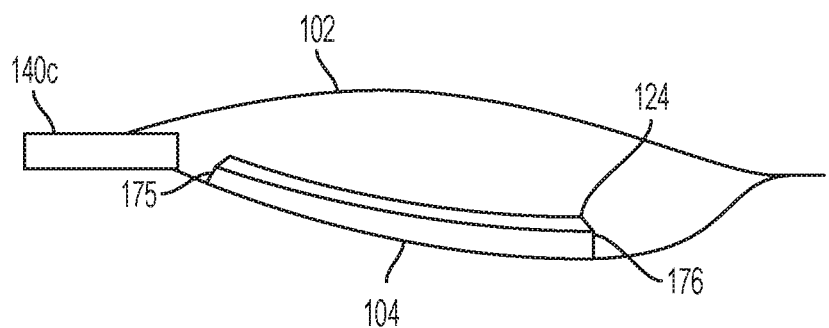
FIG. 4B is a schematic illustration showing a side view of a bioprocess bag having a channel-forming feature of FIG. 4A.

As shown in FIGS. 4A and 4B, the channel-forming feature as described herein may be a raised portion 124 which extends from an interior face of at least one of sheet 102 and sheet 104 into the interior compartment of the bioprocess bag 100. The raised portion 124 may be a textured portion of the interior face of at least one of sheet 102 and sheet 104. As used herein, the term "textured" refers to surface deformations (relative to a planar untextured sheet) as well as multiple surface regions or faces produced by uniaxial or biaxial folding, shaping, or the like that are intentionally imparted to the surface rather than merely the texture that is inherently present on the surface due to the natural topography of the surface, surface contamination, and the like. Alternatively, the raised portion 124 may be a plastic component attached, using an adhesive or via heat sealing, to the interior face of the sheet 102, 104 which is more rigid than the film or laminate of sheets 102, 104. Such plastic component may be formed from, for example, but not limited to, high density polypropylene (HDPP), polypropylene, high density polyethylene (HDPE), polyethylene, EVA, LDPE and LLDPE. While these materials do have some inherent flexibility when used to form relatively thin components or when a moderate amount of bending force is applied thereto, the raised portion 124 is distinguished from the flexible portions of the bioprocess bag 100 in that the raised portion 124 generally maintains its shape when a force is applied to dispense the contents of the bioprocess bag 100.

As shown in FIGS. 4A and 4B, the raised portion 124 may extend along any portion of the interior face of at least one of sheet 102 and sheet 104 a distance sufficient to prevent the sheets 102, 104 of the bioprocess bag 100 from sealing off portions of the bag 100 and/or from isolating the fluid and/or other components in the bag 100 from reaching an outlet. The raised portion 124 shown in FIGS. 4A and 4B extends from a first end 175 to a second end 176 along the interior face of at least one of sheet 102 and sheet 104 from approximately the top of the bioprocess bag 100 and to at least about half the distance between the top of the bioprocess bag 100 and the bottom of the bioprocess bag 100. The raised portion 124 shown in FIGS. 4A and 4B extends from approximately the top of the bioprocess bag 100 along the interior face of at least one of sheet 102 and sheet 104 and is substantially straight. However, the raised portion 124 is not so limited. The raised portion 124 as describe herein may have any shape, or may follow any path extending from approximately the top of the bioprocess bag 100 along the interior face of at least one of sheet 102 and sheet 104. For example, the raised portion 124 may extend in a curved or circuitous path from approximately the top of the bioprocess bag 100. Additionally, while the bioprocess bag 100 shown in FIGS. 4A and 4B includes one raised portion 124, bioprocess bags 100 as described herein may include any number of a plurality of raised portions 124 having any dimensions. Also, as a non-limiting example, the interior face of at least one of sheet 102 and sheet 104 may include a plurality of individual and distinct raised portions 124 of the same or varying dimensions which form a pattern on the interior face of at least one of sheet 102 and sheet 104. Such pattern may generally extend from approximately the top of the bioprocess bag 100.

As shown in FIGS. 11A and 11B, the channel-forming feature as described herein may be a tubular plastic component 1120 (such as a portion of tubing) that extends from a first end 1171 to a second end 1172. The bioprocess bag 1100 may include a plurality of inwardly facing face ports 1180, such as face ports 1180a and 1180b shown, for example, in FIGS. 11A and 11B. FIG. 11B illustrates the bioprocess bag 1100 without the tubular plastic component 1120 to more clearly show the inwardly facing face ports 1180. The inwardly facing face ports 1180 have all of the same features as the outwardly facing face ports 1140 such as illustrated in FIG. 12. In contrast to outwardly facing face ports 1140, inwardly facing face ports 1180 provide an extension 1144 into the interior compartment of the bioprocess bag 1100, but do not permit the flow of fluids and/or other components into or out of the interior compartment of the bioprocess bag 1100. Optionally, one of sheet 102 and sheet 104 may be welded, heat sealed, or otherwise adhered to the bottom surface 1154 of the base flange 1150 such that the internal fluid passage of the face ports 1180 is closed to the external side of the bioprocess bag 1100. FIG. 11A illustrates the bioprocess bag 1100 with the tubular plastic component 1120 and, as shown, the first end 1171 of the tubular plastic component 1120 may be attached to, or disposed in, an extension 1144 of one of the face ports 1180a and the second end 1172 of the tubular plastic component 1120 may be attached to, or disposed in, an extension 1144 of another of the face ports 1180b. Optionally, the first end 1171 of the tubular plastic component 1120 may be welded or sealed to the extension 1144 of one of the face ports 1180 and the second end 1172 of the tubular plastic component 1120 may be welded or sealed to the extension 1144 of another of the face ports 1180.

As shown in FIGS. 11A and 11B, at least two of the outwardly facing face ports 1140 are disposed between the inwardly facing face ports 1180. In FIG. 11A, outwardly facing face ports 1140a, 1140b, are disposed on substantially the same line with the inwardly facing face ports 1180a, 1180b, but it should be appreciated that such a configuration is not required. The outwardly facing face ports 1140a, 1140b may be disposed anywhere along the height of the bioprocess bag 1100 that is between face port 1180a and face port 1180b so long as the channel-forming feature can form a conduit which cannot be closed off by exertion of a pressure on sheets 102, 104 as the bioprocess bag 1100 collapses. The distance between face port 1180a and face port 1180b is sufficient to prevent the sheets 102, 104 of the bioprocess bag 1100 from sealing off portions of the bag 1100 and/or from isolating the fluid and/or other components in the bag 1100 from reaching an outlet. According to embodiments of the present disclosure, the distance between face port 1180a and face port 1180b may be at least about half the height of the bioprocess bag 1100. In other words, the distance between face port 1180a and face port 1180b may be at least about half the length of the sheets 102, 104 of the bioprocess bag 1100, but preferably less than the full length of the sheets 102, 104 of the bioprocess bag 1100. For example, where the length of the sheets 102, 104 is represented by "L", the distance between face port 1180a and face port 1180b may be between about 0.5 L and about 0.95 L, or between about 0.5 L and about 0.85 L, or even between about 0.5 L and about 0.75 L.

Figure 7:
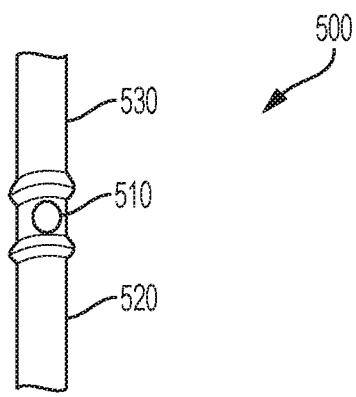
FIG. 7 illustrates an exemplary channel-forming feature extender in accordance with embodiments of the present disclosure.
Figure 8:
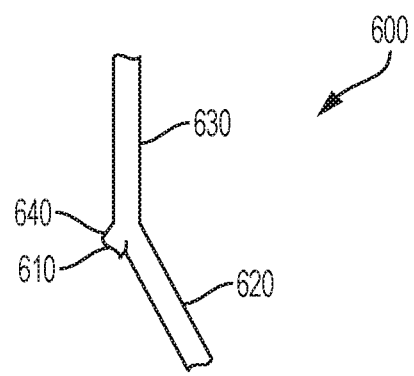
FIG. 8 illustrates an exemplary channel-forming feature extender in accordance with embodiments of the present disclosure.
Figure 9:
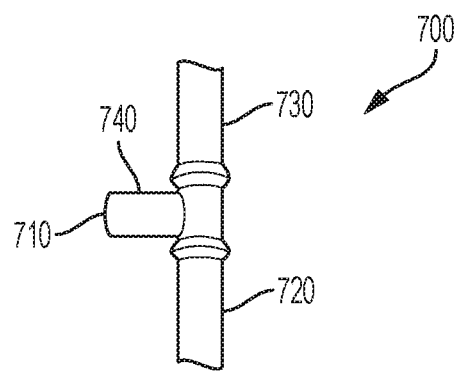
FIG. 9 illustrates an exemplary channel-forming feature extender in accordance with embodiments of the present disclosure.

FIGS. 7-9 illustrate exemplary channel-forming feature extenders which are configured to receive, or be otherwise associated with, a channel-forming feature as described herein. Each of the channel-forming feature extenders shown in FIGS. 7-9 are plastic components which extend from a first end to a second end, the second end being disposed in the interior compartment of the bioprocess bag 100. The first end of extender 500, 600, 700 is configured to be attached to, or disposed in, at least one of the plurality of connectors 140 or attached to, or disposed in, at least one of the plurality of ports 42 of a port fitment 40. Each of extenders 500, 600, 700 includes an opening 510, 610, 710 disposed between the first end and the second end of the channel-forming feature 500, 600, 700. Each of extenders 500, 600, 700 also includes a lower extension 520, 620, 720 which extends between the opening 510, 610, 710 and the second end. As will be described in greater detail below, the lower extension 520, 620, 720 is configured to receive, or be otherwise associated with, a channel-forming feature such as solid extruded plastic component 120 shown in FIGS. 1 and 2A-2C, or tubular plastic component 122 shown in FIGS. 3A-3C. Each of extenders 500, 600, 700 also includes an upper extension 530, 630, 730 which extends between the opening 510, 610, 710 and the first end and which has an interior channel which fluidly connects the opening 510, 610, 710 to the at least one connection apparatus of the bioprocess bag 100. Extenders 600, 700 also include side extensions 640, 740 which include interior channels that fluidly connect the opening 610, 710 and the interior channel of the upper extension 630, 730. Generally, the extenders as described herein further facilitate providing a fluid flow path for the contents of the bioprocess bag 100 to reach an outlet.

The channel-forming feature extender 500 shown in FIG. 7 is a straight component that includes an opening 510 formed in a sidewall. The opening 510 is positioned between the lower extension 520 and the upper extension 530. The upper extension 530 includes an interior channel which fluidly connects the opening 510 to the at least one connection apparatus of the bioprocess bag 100. The lower extension 520 may be a solid portion of the channel-forming feature 500, or may also include an interior channel. A channel-forming feature, such as tubular plastic component 122, may be attached to the lower extension 520. Where the lower extension 520 includes an interior channel, the end of the lower extension 520 remote from the opening 510 may be a closed end, or may include a plug inserted in the end to prevent fluid and/or other components from flowing into the interior channel. Optionally, a channel-forming feature, such as solid extruded plastic component 120 may be disposed in the interior channel of the lower extension 520.

The channel-forming feature extender 600 shown in FIG. 8 is a Y-component where one of the legs of the Y is the lower extension 620 and the other leg of the Y is the side extension 640. The side extension 640 may be shorter in length than the lower extension 620 and includes opening 610 formed in the end of side extension 640. The upper extension 630 includes an interior channel which fluidly connects the opening 610 via the interior channel of the side extension 640 to the at least one connection apparatus of the bioprocess bag 100. The lower extension 620 may be a solid portion of the channel-forming feature 600, or may also include an interior channel. A channel-forming feature, such as tubular plastic component 122, may be attached to the lower extension 620. Where the lower extension 620 includes an interior channel, the end of the lower extension 620 remote from the intersection of extensions 620, 630, 640 may be a closed end, or may include a plug inserted in the end to prevent fluid and/or other components from flowing into the interior channel. Optionally, a channel-forming feature, such as solid extruded plastic component 120 may be disposed in the interior channel of the lower extension 620.

The channel-forming feature extender 700 shown in FIG. 9 is a Tee-component having a side extension 740 extending at a 90 degree angle from the lower extension 720 and the upper extension 730 which together form a straight portion of the feature 700. The side extension 740 includes opening 710 formed in the end of side extension 740. The upper extension 730 includes an interior channel which fluidly connects the opening 710 via the interior channel of the side extension 740 to the at least one connection apparatus of the bioprocess bag 100. The lower extension 720 may be a solid portion of the channel-forming feature 700, or may also include an interior channel. A channel-forming feature, such as tubular plastic component 122, may be attached to the lower extension 720. Where the lower extension 720 includes an interior channel, the end of the lower extension 720 remote from the intersection of the various extensions may be a closed end, or may include a plug inserted in the end to prevent fluid and/or other components from flowing into the interior channel. Optionally, a channel-forming feature, such as solid extruded plastic component 120 may be disposed in the interior channel of the lower extension 720.

According to embodiments of the present disclosure, the channel-forming feature is arranged in the bioprocess bag 100, 1100 to allow for the fluid flow path provided by the channel-forming feature to be in fluid communication with the outlet. Referring again to FIG. 2A as one example, the connector 140c nearest the channel-forming feature, in this case a solid extruded plastic component 120, is preferably an outlet and any of the other of the plurality of connectors 140a, 140b may be an inlet. Where two or more of the plurality of the connectors 140 are located a similar distance from the channel-forming feature, any of the plurality of the connectors 140 which the channel-forming feature can be maintain in fluid connection with the interior compartment of bioprocess bag 100 may be an outlet. As will be understood from the discussion herein, it should be appreciated that a similar arrangement applies when the channel-forming feature is any of solid extruded plastic component 120, a tubular plastic component 122, a raised portion 124, or any other feature that prevents the bioprocess bag 100 from closing on itself, thus providing a fluid flow path for the contents of the bag 100 to reach the outlet. As exemplified in FIG. 2B, as the bioprocess bag 100 collapses, the channel-forming feature forms a conduit which cannot be closed off by exertion of a pressure on sheets 102, 104 of the bioprocess bag 100. Thus, the entire interior compartment of the bioprocess bag 100 remains in fluid communication with the outlet at all times. Similarly, with reference to FIGS. 3A and 3B, where the at least one connection apparatus is a port fitment 40 as described herein, at least one of a plurality of ports 42 includes the channel-forming feature attached to, or disposed within, the port 42. Such arrangement also allows the channel-forming feature to form a conduit which cannot be closed off by exertion of a pressure on sheets 102, 104 as the bioprocess bag 100 collapses. FIG. 2C is a schematic illustration showing a top view of the bioprocess bag having a channel-forming feature such as is shown in FIGS. 2A and 2B. FIG. 2C illustrates that the channel-forming feature, in this illustration the extruded plastic component 120, prevents sheets 102, 104 from collapsing to a point where the entire face of one sheet 102 is contacted by the other sheet 104 which prevents the sheets 102, 104 from sealing off portions of the bag 100 and/or from isolating the fluid and/or other components in the bag 100 from reaching an outlet. As is clearly shown in FIG. 2C, a fluid flow path around the outside of the channel-forming feature is always maintained.

The bioprocess bag 100, 1100 also includes at least one hole 150 punched in the top welded edge of the bioprocess bag 100, 1100 and at least one hole 150 punched in the bottom welded edge of the bioprocess bag 100, 1100. The holes 150 allow for the bioprocess bag 100, 1100 to be mounted in a hanging position from either the top or the bottom of the bag 100, 1100 as will be described further below. Optionally, the bioprocess bag 100, 1100 may include at least one rigid rod (not shown) sealed within the top welded edge of the bioprocess bag 100, 1100 and at least one rigid rod (not shown) sealed within the bottom welded edge of the bioprocess bag 100, 1100. Similar to the holes 150, the rigid rods allow for the bioprocess bag 100, 1100 to be mounted in a hanging position from either the top or the bottom of the bag 100, 1100.

According to embodiments of the present disclosure, the bioprocess bag 100 may include chromatography resin in the interior compartment of the bag 100. The chromatography resin may include, but is not limited to: synthetic based resins, such as styrene-DVB; organic polymer-based resins, such as agarose or dextran; or inorganic resins, such as silica. The chromatography resin may include ligands, such as affinity ligands, ion exchange ligands, hydrophobic interaction chromatography (HIC) ligands, chelating ligands, thiophilic ligands or multimodal ligands.

According to embodiments of the present disclosure, the bioprocess bag 100, 1100 may also include a sealable opening 160 which can be used to fill the bag 100 with chromatography resin. As shown, for example in FIG. 2A, the sealable opening 160 may be formed in a face of at least one of sheets 102, 104. The sealable opening 160 may be in the form of a port having a collar which can be sealed and unsealed by a sealing cap. The sealable opening 160 may be fabricated using sealing techniques which are known to persons skilled in the art. The sealing cap may be a threaded screw cap having internal threads that engage external threads of the collar to twist the cap into the collar. A gasket may also be provided in order to provide a fluid-tight seal between the collar and the cap.

Figure 10:
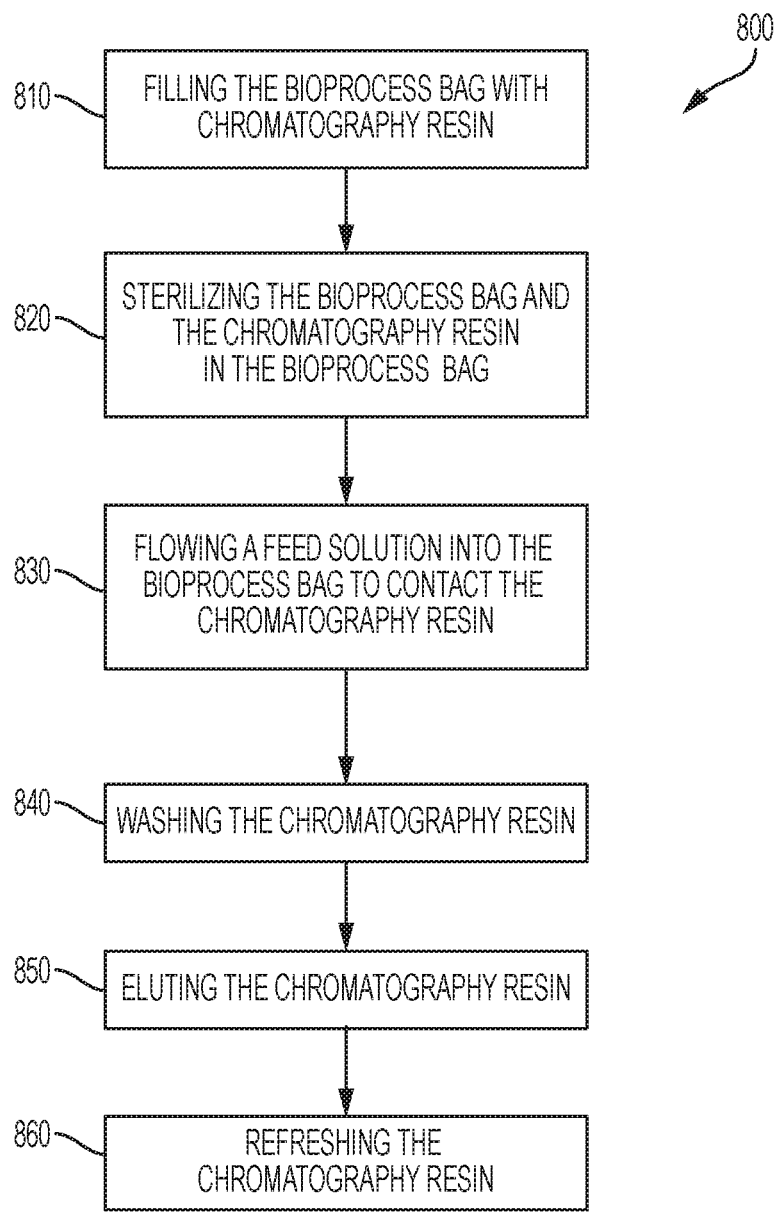
FIG. 10 is a flow chart illustrating a method in accordance with embodiments of the present disclosure

Provided are also methods for separating at least one target compound from a feed solution in bioprocess bags as described herein. FIG. 10 is a flow chart illustrating a method 800 as described herein. It should be appreciated that FIG. 10 is merely illustrative of embodiments of the methods described herein, that not all of the steps shown need be performed, and that steps of embodiments of the methods described herein need not be performed in any particular order except where an order is specified.

The method may include a step 810 of filling the bioprocess bag 100, 1100 with chromatography resin. Filling the bioprocess bag 100, 1100 may include unsealing the sealable opening 160 and adding chromatography resin through the opening 160 and into the interior compartment of the bioprocess bag 100, 1100. Optionally, once chromatography resin has been added and the sealable opening 160 is resealed, the method may further include a step 820 of sterilizing the chromatography resin in the bioprocess bag 100, 1100. Such sterilizing may be completed using autoclaving, gamma sterilization or any other known sterilization process. Once filled, the bioprocess bag 100, 1100 may be aseptically stored or transported to a location near a cell culture vessel such as, for example, a bioreactor or other holding vessel.

According to embodiments of the present disclosure, the bioprocess bag 100, 1100 and the chromatography resin may be sterilized separately and the step 810 of filling the bioprocess bag 100, 1100 with chromatography resin may include adding chromatography resin into the interior compartment of the bioprocess bag 100, 1100 in a sterile environment. Additionally, the chromatography resin may be added to the interior compartment of the bioprocess bag 100, 1100 through openings other than the sealable opening 160 as described above. Alternatively, the chromatography resin may be added to the interior compartment of the bioprocess bag 100, 1100 through at least one of the connection apparatuses.

The method may further include a step 830 of flowing a feed solution into the bioprocess bag 100, 1100 to contact the chromatography resin in the bioprocess bag 100, 1100. The feed solution may be any fluid mixture, for example a fermentation broth from a cell culture vessel such as a bioreactor, which contains two or more compounds to be separated. In this context, the term "compound" is used in a broad sense for any entity such as a molecule, chemical compound, cell, etc. The feed solution may not be passed directly from the cell culture vessel. Instead the feed solution may be subjected to one or more steps or pre-treatment such as filtration prior to flowing the feed solution into the bioprocess bag 100, 1100. Flowing a feed solution into the bioprocess bag 100, 1100 may include adding the feed solution to the bioprocess bag 100, 1100 through at least one of the connection apparatuses to contact the feed solution with the chromatography resin. Contact with the chromatography resin results in binding of target compounds in the feed solution with the chromatography resin. As used herein, the term "target compound" refers to any compound which is to be separated from the feed solution. It should be appreciated that a target compound may be a desired product such as, for example, a drug, diagnostic or vaccine, or in the alternative, a target compound may be a contaminant or a compound generally considered as an undesirable product which is to be removed from one or more desired products. The chromatography resin is chosen such that functional groups of the ligands are capable of binding target compounds, for example, via a "lock/key" mechanism, such as antibody/antigen; enzyme/receptor; biotin/avidin, etc. The target compounds may be, but are not limited to, proteins, such as membrane proteins or antibodies, e.g. monoclonal antibodies, fusion proteins comprising antibody or antibody fragments, such as Fab-fragments, and recombinant proteins; peptides; nucleic acids, such as DNA or RNA, e.g. oligonucleotides, plasmids, or genomic DNA; cells, such as prokaryotic or eukaryotic cells or cell fragments; virus; prions; carbohydrates; lipids etc.

Optionally, flowing a feed solution into the bioprocess bag 100, 1100 may be performed any number of times. For example, a first volume of feed solution may be added to the bioprocess bag 100, 1100 to contact the chromatography resin. After a period of time sufficient for binding of target compounds in the feed solution with the chromatography resin, the first volume of feed solution may be dispensed from the bioprocess bag 100, 1100, such as through at least one of the connection apparatuses, and a subsequent volume of feed solution may be added to the bioprocess bag 100, 1100 to contact the chromatography resin. Additional volumes of feed solution may be added to the bioprocess bag 100, 1100 until the binding capacity of the chromatography resin is reached.

The method may further include a step 840 of washing the chromatography resin. A wash solution may be added to the bioprocess bag 100, 1100 through at least one of the connection apparatuses to contact the wash solution with the chromatography resin. The wash solution may include, for example, a buffer. Washing the chromatography resin is performed in conditions which provide for substantially all of the target compounds to remain bound to the chromatography resin while compounds not bound to the chromatography resin enter the wash solution. Once contacted with the wash solution, the density of the chromatography resin allows for settling of the chromatography resin and formation of at least two separate phases, with the lowest of the at least two separate phases containing the chromatography resin. After a sufficient amount of settling has occurred, washing the chromatography resin may further include dispensing the less dense upper phases through the at least one of the connection apparatuses. Dispensing the less dense upper phases may include using a peristaltic pump to pump the less dense upper phases out of the bioprocess bag 100, 1100. Alternatively, dispensing the less dense upper phases includes applying a pressure to the outside of the bioprocess bag 100, 1100 to push the less dense upper phases out of the bioprocess bag 100, 1100. Optionally, adding the wash solution and dispensing the less dense upper phases may be performed any number of times.

The method may further include a step 850 of eluting the chromatography resin. Eluting the chromatography resin may include adding an eluent solution, such as a solvent, capable of releasing the target compounds from the chromatography resin. The eluent solution may be added to the bioprocess bag 100, 1100 through at least one of the connection apparatuses to contact the eluent solution with the chromatography resin. Eluting the chromatography resin is performed in conditions which provide for substantially all of the target compounds to be released from the chromatography resin and enter the eluent solution. Once contacted with the eluent solution, the density of the chromatography resin allows for settling of the chromatography resin and formation of at least two separate phases, with the lowest of the at least two separate phases containing the chromatography resin. After a sufficient amount of settling has occurred, eluting the chromatography resin may further include dispensing the less dense upper phases through the at least one of the connection apparatuses. Dispensing the less dense upper phases may include using a peristaltic pump to pump the less dense upper phases out of the bioprocess bag 100, 1100. Alternatively, dispensing the less dense upper phases includes applying a pressure to the outside of the bioprocess bag 100, 1100 to push the less dense upper phases out of the bioprocess bag 100, 1100. Optionally, adding the eluent solution and dispensing the less dense upper phases may be performed any number of times.

It should be appreciated that, according to embodiments of the present disclosure, the step of the method at which the desired product is removed from the bioprocess bag 100, 1100 will depend on the conditions selected for the separation method. For example, the desired product may be the target compound and may be removed from the bioprocess bag 100, 1100 in the eluent solution. Alternatively, the desired product may not be the target compound and may be removed from the bioprocess bag 100, 1100 in the wash solution. As yet another alternative, two or more products may be desired products. For example, the user may collect a compound that is not a target compound in the wash solution as a first desired product and may also collect the target compound as a second desired product. According to embodiments of the present disclosure, any of the compounds in the feed solution may be considered the desired product and it is ultimately within the user's discretion which compounds to collect for later use or processing and which compounds to discard.

The method may further include a step 860 of refreshing the chromatography resin. Refreshing the chromatography resin may include adding a buffer to the bioprocess bag 100, 1100 to prepare the chromatography resin to repeat the previous steps of the method described herein where another feed solution is added to the bioprocess bag 100, 1100. Alternatively, the bioprocess bag 100, 1100 may be disposed of following eluting the chromatography resin without refreshing the chromatography resin.

According to embodiments of the present disclosure, any of the steps of method 800 described herein may include agitating the bioprocess bag 100, 1100 on a shaking platform, vibrating platform, or rocking platform. Agitating the bioprocess bag 100, 1100 in conjunction with the step 830 of flowing a feed solution into the bioprocess bag 100, 1100 may allow for efficient mixing of the feed solution and the chromatography resin which may in turn improve the rate of binding of target compounds in the feed solution with the chromatography resin. Agitating the bioprocess bag 100, 1100 in conjunction with the step 840 of washing the chromatography resin may allow for efficient mixing of the wash solution and the chromatography resin which may in turn improve the rate of washing. Agitating the bioprocess bag 100, 1100 in conjunction with the step 850 of eluting the chromatography resin may allow for efficient mixing of the eluent solution and the chromatography resin which may in turn improve the rate of release of target compounds from the chromatography resin.

According to an aspect (1) of the present disclosure, a method for separating at least one target compound from a feed solution. The method comprises: filling a bioprocess package with a chromatography resin, the bioprocess package comprising: a 2D flexible container comprising an interior compartment, a height having an upper half and a lower half, an inlet and an outlet, the inlet and the outlet being disposed on the same half of the 2D flexible container; and a channel-forming feature in the interior compartment of the container, the channel-forming feature being configured to maintain a fluid flow path that fluidly connects the interior compartment of the flexible container with the outlet; flowing a feed solution into the bioprocess package to contact the chromatography resin such that substantially all of the at least one target compound binds to the chromatography resin; washing the chromatography resin in the bioprocess package; and eluting the chromatography resin such that substantially all of the at least one target compound is released from the chromatography resin.

According to an aspect (2) of the present disclosure, the method of aspect (1) is provided, wherein filling a bioprocess package with a chromatography resin comprises adding chromatography resin to the interior compartment of the bioprocess package.

According to an aspect (3) of the present disclosure, the method of any of aspects (1)-(2) is provided, wherein the feed solution comprises two or more compounds to be separated.

According to an aspect (4) of the present disclosure, the method of any of aspects (1)-(3) is provided, wherein the chromatography resin comprises ligands capable of binding the target compounds.

According to an aspect (5) of the present disclosure, the method of any of aspects (1)-(4) is provided, wherein washing the chromatography resin comprises adding a wash solution to the bioprocess package, the wash solution comprising a buffer.

According to an aspect (6) of the present disclosure, the method of any of aspects (1)-(5) is provided, wherein washing the chromatography resin comprises forming at least two liquid phases having different densities and dispensing the less dense upper liquid phases from the bioprocess package.

According to an aspect (7) of the present disclosure, the method of aspect (6) is provided, wherein the most dense liquid phase comprises the chromatography resin having the at least one target compound bound thereto.

According to an aspect (8) of the present disclosure, the method of any of aspects (1)-(7) is provided, wherein eluting the chromatography resin comprises forming at least two liquid phases having different densities and dispensing the less dense upper liquid phases from the bioprocess package.

According to an aspect (9) of the present disclosure, the method of aspect (8) is provided, wherein the less dense upper liquid phases comprise the at least on target compound.

According to an aspect (10) of the present disclosure, the method of any of aspects (1)-(9) is provided, further comprising sterilizing the chromatography resin in the bioprocess package.

According to an aspect (11) of the present disclosure, the method of any of aspects (1)-(10) is provided, further comprising refreshing the chromatography resin.

According to an aspect (12) of the present disclosure, the method of aspect (11) is provided, wherein refreshing the chromatography resin comprises adding a buffer to the bioprocess package.

According to an aspect (13) of the present disclosure, the method of any of aspects (1)-(12) is provided, further comprising agitating bioprocess package.

According to an aspect (14) of the present disclosure, the method of any of aspects (1)-(13) is provided, wherein the 2D flexible container comprises two sheets hermetically sealed along edges of the two sheets to form the interior compartment.

According to an aspect (15) of the present disclosure, the method of aspect (14) is provided wherein the two sheets comprise a film or laminate comprising a polymeric material selected from a group consisting of polyethylene (PE), polypropylene (PP), polyvinyl chloride (PVC), polyethylene terephtalate (PET), polystyrene (PS), polycarbonate (PC), polymethylpentene (PMP), polyetheretherketone (PEEK) polytetrafluoroethylene (PTFE), polyfluoroalkoxy (PFA), polychlorotrifluoroethylene (PCTFE), ethylene vinyl acetate (EVA), and derivatives thereof.

According to an aspect (16) of the present disclosure, the method of any of aspects (1)-(15) is provided, wherein the inlet and the outlet comprise connectors having an internal fluid passage that permits the flow of fluids and/or other components into or out of the interior compartment of the flexible container.

According to an aspect (17) of the present disclosure, the method of any of aspects (1)-(16) is provided, wherein the connectors comprise a face port.

According to an aspect (18) of the present disclosure, the method of any of aspects (1)-(17) is provided, wherein the channel-forming feature comprises a solid extruded plastic component.

According to an aspect (19) of the present disclosure, the method of aspect (18) is provided, wherein the solid extruded plastic component is welded into a seam of the flexible container.

According to an aspect (20) of the present disclosure, the method of any of aspects (1)-(17) is provided, wherein the channel-forming feature comprises a tubular plastic component.

According to an aspect (21) of the present disclosure, the method of aspect (20) is provided, wherein the tubular plastic component is welded into a seam of the flexible container.

According to an aspect (22) of the present disclosure, the method of aspect (20) is provided further comprising at least two inwardly facing face ports, wherein a first end of the tubular plastic component is attached to one of the at least two inwardly facing face ports and a second end of the tubular plastic component is attached to another of the at least two inwardly facing face ports.

According to an aspect (23) of the present disclosure, the method of any of aspects (1)-(17) is provided, wherein the channel-forming feature comprises a raised portion which extends from an interior face of at least one of the two sheets.

According to an aspect (24) of the present disclosure, the method of aspect (23) is provided, wherein the raised portion comprises a plastic component attached to the interior face of the at least one of the two sheets.

According to an aspect (25) of the present disclosure, the method of aspect (23) is provided, wherein the raised portion comprises a textured portion of the interior face of the at least one of the two sheets.

While the present disclosure includes a limited number of embodiments, those skilled in the art, having benefit of this disclosure, will appreciate that other embodiments can be devised which do not depart from the scope of the present disclosure.

What is claimed is:

1. A method for separating at least one target compound from a feed solution, the method comprising:
 filling a bioprocess package with a chromatography resin, the bioprocess package comprising:
  a 2D flexible container comprising an interior compartment, a height having an upper half and a lower half, an inlet and an outlet, the inlet and the outlet being disposed on the same half of the 2D flexible container; and
  a channel-forming feature in the interior compartment of the container, the channel-forming feature being configured such that a fluid flow path provided by the channel-forming feature is in fluid communication with the outlet;

wherein the channel-forming feature is on the same half of the 2D flexible container as the outlet; and wherein the channel-forming feature and the outlet are separate components;

flowing a feed solution into the bioprocess package to contact the chromatography resin such that substantially all of the at least one target compound binds to the chromatography resin;

washing the chromatography resin in the bioprocess package; and eluting the chromatography resin such that substantially all of the at least one target compound is released from the chromatography resin.

2. The method of claim 1, wherein filling a bioprocess package with a chromatography resin comprises adding chromatography resin to the interior compartment of the bioprocess package.

3. The method of claim 1, wherein the feed solution comprises two or more compounds to be separated.

4. The method of claim 1, wherein the chromatography resin comprises ligands capable of binding the target compounds.

5. The method of claim 1, wherein washing the chromatography resin comprises adding a wash solution to the bioprocess package, the wash solution comprising a buffer.

6. The method of claim 1, wherein washing the chromatography resin comprises forming at least two liquid phases having different densities and dispensing the less dense upper liquid phases from the bioprocess package.

7. The method of claim 6, wherein the most dense liquid phase comprises the chromatography resin having the at least one target compound bound thereto.

8. The method of claim 1, wherein eluting the chromatography resin comprises forming at least two liquid phases having different densities and dispensing the less dense upper liquid phases from the bioprocess package.

9. Method of claim 8, wherein the less dense upper liquid phases comprise the at least one target compound.

10. The method of claim 1, further comprising sterilizing the chromatography resin in the bioprocess package.

11. The method of claim 1, further comprising refreshing the chromatography resin.

12. The method of claim 11, wherein refreshing the chromatography resin comprises adding a buffer to the bioprocess package.

13. The method of claim 1, further comprising agitating the bioprocess package.

14. The method of claim 1, wherein the 2D flexible container comprises two sheets hermetically sealed along edges of the two sheets to form the interior compartment.

15. The method of claim 14, wherein the two sheets comprise a film or laminate comprising a polymeric material selected from a group consisting of polyethylene (PE), polypropylene (PP), polyvinyl chloride (PVC), polyethylene terephtalate (PET), polystyrene (PS), polycarbonate (PC), polymethylpentene (PMP), polyetheretherketone (PEEK) polytetrafluoroethylene (PTFE), polyfluoroalkoxy (PFA), polychlorotrifluoroethylene (PCTFE), ethylene vinyl acetate (EVA), and derivatives thereof.

16. The method of claim 1, wherein the inlet and the outlet comprise connectors having an internal fluid passage that permits the flow of fluids and/or other components into or out of the interior compartment of the flexible container.

17. The method of claim 1, wherein the channel-forming feature comprises a solid extruded plastic component.

18. The method of claim 17, wherein the solid extruded plastic component is welded into a seam of the flexible container.

19. The method of claim 1, wherein the channel-forming feature comprises a tubular plastic component.

20. The method of claim 19, wherein the tubular plastic component is welded into a seam of the flexible container.

21. The method of claim 19 further comprising at least two inwardly facing face ports, wherein a first end of the tubular plastic component is attached to one of the at least two inwardly facing face ports and a second end of the tubular plastic component is attached to another of the at least two inwardly facing face ports.

22. The method of claim 1, wherein the channel-forming feature comprises a raised portion which extends from an interior face of at least one of the two sheets.

23. The method of claim 22, wherein the raised portion comprises a plastic component attached to the interior face of the at least one of the two sheets.

24. The method of claim 22, wherein the raised portion comprises a textured portion of the interior face of the at least one of the two sheets.

* * * * *